(12) United States Patent
Sanner

(10) Patent No.: US 7,264,780 B1
(45) Date of Patent: Sep. 4, 2007

(54) DEVICE FOR TAKING AND EXAMINING SAMPLES

(75) Inventor: Stefan Sanner, Germering (DE)

(73) Assignee: Oxoid (Ely) Limited, Cambridgeshire (GB)

( * ) Notice: Subject to any disclaimer, the term of this patent is extended or adjusted under 35 U.S.C. 154(b) by 0 days.

(21) Appl. No.: 09/446,323

(22) PCT Filed: Jun. 19, 1998

(86) PCT No.: PCT/EP98/03764

§ 371 (c)(1),
(2), (4) Date: Mar. 20, 2000

(87) PCT Pub. No.: WO98/58587

PCT Pub. Date: Dec. 30, 1998

(30) Foreign Application Priority Data

Jun. 20, 1997 (DE) ................. 197 26 268

(51) Int. Cl.
*G01N 31/22* (2006.01)
(52) U.S. Cl. ................ 422/101; 422/58; 422/102
(58) Field of Classification Search ........... 422/85, 422/58, 60, 68.1, 82.05, 99, 102, 101, 103, 422/55, 56, 57; 435/287.1, 810; 436/164, 436/169, 178; 73/864.71, 864, 863.85
See application file for complete search history.

(56) References Cited

U.S. PATENT DOCUMENTS

| | | | |
|---|---|---|---|
| 4,269,237 A * | 5/1981 | Berger ................. 137/539 |
| 4,534,939 A * | 8/1985 | Smith et al. ............. 422/61 |
| 4,604,360 A * | 8/1986 | Hounsell ............... 422/236 |
| 4,770,853 A * | 9/1988 | Bernstein .............. 422/102 |
| 4,848,167 A | 7/1989 | Gordon et al. |
| 4,978,504 A | 12/1990 | Nason |
| 5,096,669 A * | 3/1992 | Lauks et al. ......... 204/403.02 |
| 5,215,713 A | 6/1993 | Steinbiss |
| 5,256,537 A * | 10/1993 | Phillips et al. ........... 222/80 |
| 5,283,038 A | 2/1994 | Seymour |
| 5,393,496 A | 2/1995 | Seymour |
| 6,048,735 A * | 4/2000 | Hessel et al. ............ 436/518 |

FOREIGN PATENT DOCUMENTS

| | | |
|---|---|---|
| AU | 376 117 | 10/1984 |
| CH | 474 060 | 7/1969 |
| CH | 635 937 | 4/1983 |
| DE | 25 37 013 | 6/1976 |
| DE | 34 27 114 | 1/1986 |
| DE | 300 372 | 6/1992 |
| DE | 41 17 635 | 12/1992 |
| EP | 0 396 016 | 11/1990 |
| EP | 0 520 408 | 12/1992 |
| EP | 0 727 653 | 8/1996 |
| WO | WO94/11107 | 5/1994 |
| WO | WO95/08761 | 3/1995 |
| WO | WO96/14570 | 5/1996 |

* cited by examiner

*Primary Examiner*—Jill Warden
*Assistant Examiner*—Paul Hyun
(74) *Attorney, Agent, or Firm*—Nixon Peabody LLP; Jeffrey A. Lindeman

(57) ABSTRACT

The invention relates to a device for taking and examining samples, comprising a tube-shaped housing (50) in which a cartridge (30), a testing means (40) and a sample-taking means (10) are positioned, wherein a sample introduced by means of the sample-taking means (10) can be mixed with a content of the cartridge (30), and the testing means (40) is used to analyze the sample mixture.

7 Claims, 5 Drawing Sheets

DEVICE FOR TAKING AND EXAMINING SAMPLES

CROSS-REFERENCES TO RELATED APPLICATIONS

The present application is a national stage application of PCT/EP98/03764, filed Jun. 19, 1998, which, in turn, claims priority benefit to German application 197 26 268.6, filed Jun. 20, 1997, the entire disclosures of which are all hereby incorporated by reference.

FIELD OF THE INVENTION

The present invention relates to a device for taking and examining samples, in particular for the integrated taking of samples and examination by means of test methods, in particular immunobiological, chemical or biochemical kinds of tests.

BACKGROUND OF THE INVENTION

DE-C2-41 I7 635 describes a multi-purpose examination device for fecal samples. This device comprises a housing with a cavity and a laterally arranged tube. A fecal sample Is taken up by means of a stirring portion and introduced into the cavity, and this cavity is closed by means of a cap. An inner connection of the tube is wetted with the fecal sample. By means of a syringe, a highly sensitive reagent, such as o-toluidine or tetramethyl benzhydrine and hydrogen peroxide is introduced into the cavity. Due to a color reaction it is tested whether the taken fecal sample contains traces of blood. For a further test, a slightly sensitive test reagent such as guaiac resin or lignum vitae resin and hydrogen peroxide are introduced through an opening at the free end of the tube. By observing a corresponding color reaction ft Is examined whether the fecal sample contains traces of blood. This examination device has a complicated design comprising a plurality of individual parts, and use thereof is difficult.

EP-A2-O 327 144 describes a sample taking container and a method for processing a pasty sample material. A sample taking cup for taking a sample and introducing it into the sample-taking container is arranged at the cover of a container by means of a shaft. A liquid for suspending the fecal sample is contained in the sample-taking container. After introducing the sample cup and subsequently screwing on the container cover, the fecal sample disperses in the liquid. After transportation into a laboratory, the container cover is removed and a second liquid, in particular an organic solvent (ether or ethyl acetate) or colorant (e.g. Lugol's solution) is added. For the subsequent filtration, a separate filter body is screwed on, and by shaking the filtered suspension is obtained in the filtrate container. The filtered suspension can then be examined. This device comprises a plurality of individual parts, and use thereof is difficult. In particular, there is a danger that the liquid is spilled during use of the device.

U.S. Pat. No. 4,978,504 describes a test unit for taking and analyzing samples. The test unit comprises a holder, and at one end of a small rod a taking sponge is arranged by means of which a sample can be taken. The holder comprises a cavity In which a destroyable ampulla containing a reaction fluid is provided. After taking a sample, the small rod Is introduced into a tube-shaped housing, and the holding means is attached. Then, the ampulla is destroyed by impressing the holding means and the reaction fluid flows into the housing and comes In contact with the sample. Then the mixture is collected in a container or dropped onto a carrier and examined by means of separate devices.

EPA-0 520 408 describes a device which is suitable in particular for examining saliva samples. This test unit includes a cylindrical container containing a liquid and a sample collector shaped as a piston with a sponge arranged thereto for taking a saliva sample. After taking a sample, the sample collector is introduced into the housing and the sample collector sponge comes in contact with the liquid. The test device also comprises a collection container which can be attached to the other end of the housing and is displaceable with respect to the housing. In the interior of the collection container a thorn is arranged opposite of an opening at the other end of the housing, width opening is closed by a foil or sheet. In the attached position of the collection container, the foil or sheet is destroyed by the thorn and thus the opening is free. By introducing the piston-shaped sample collector completely, the liquid is pressed from the container into the collection container, and at the same time the sponge-like sample collector is pressed out. The collection container contains a reaction substance which reacts with the sample and the liquid, wherein this liquid is subsequently examined by means of a separate device. U.S. Pat. No. 5,393,496 describes a similar test device.

BRIEF SUMMARY OF THE INVENTION

It is an object of the present invention to provide a device for. taking and examining samples which is designed in a simple manner and can be handled easily.

This object is achieved with the features of the claims. It is a particular advantage of the device of the present invention that the samples can be taken easily, that the sample-taking means containing the sample can be safely introduced into a housing and can be mixed therein in a simple manner with a sample reprocessing liquid and that then the sample can be examined by means of a testing means arranged in the housing.

A further advantage of the device according to the invention Is that a sample reprocessing liquid is safely sealed in the cartridge and that the user does not come in contact with the sample also after mixing.

BRIEF DESCRIPTION OF THE DRAWINGS

In the following, the invention is explained in more detail on the basis of an embodiment and by referring to the drawings in which.

DETAILED DESCRIPTION OF THE INVENTION

Figure 1:
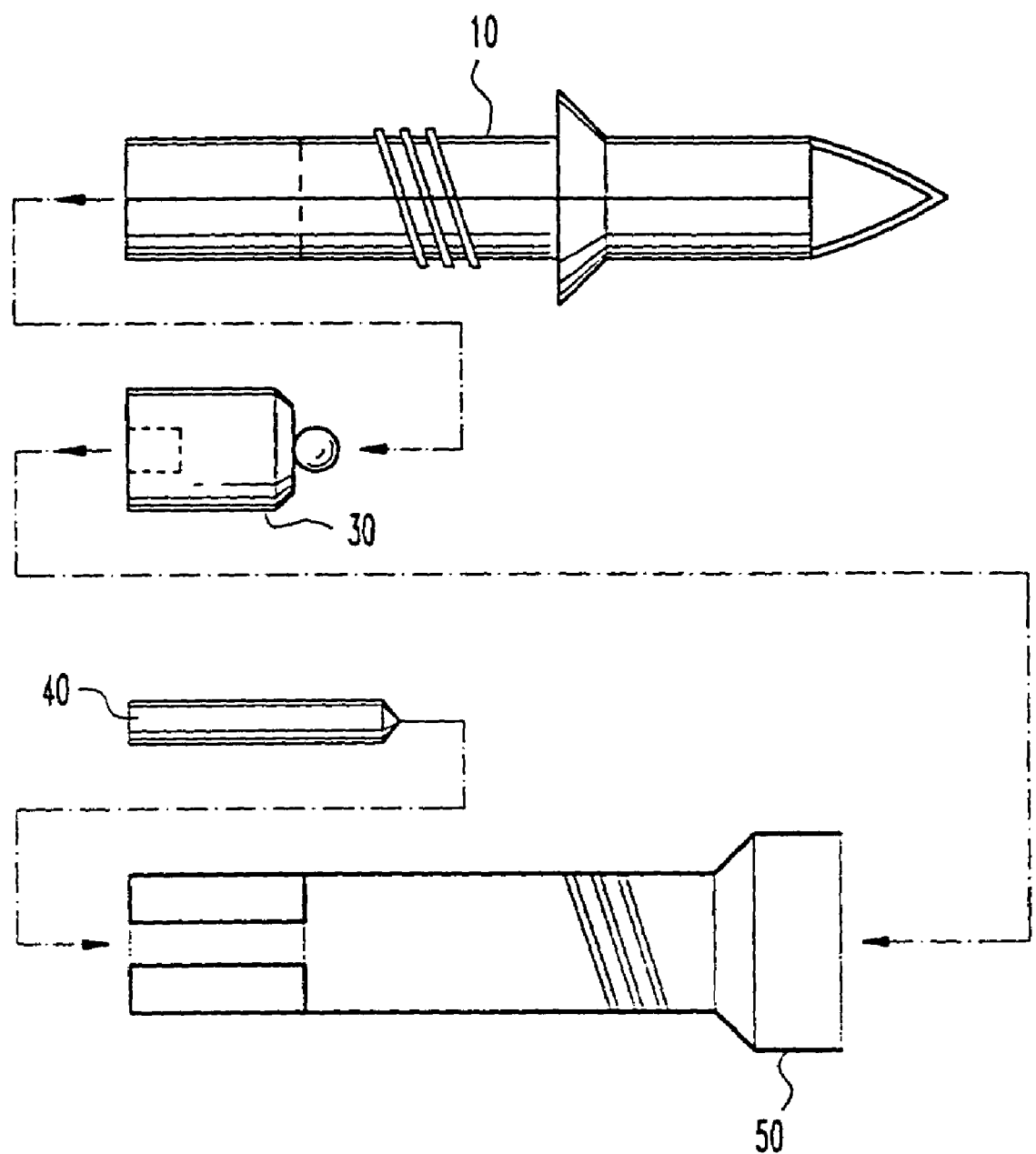
FIG. 1 is a basic sketch of the construction of a device according to the Invention, FIG. 2 a partial view of an embodiment of a sample-taking means according to the invention seen from the handle, FIG. 3 a partial view of the sample-taking means according to FIG. 2 seen from the sample, FIG. 4 a basic sketch of the device according to the invention, and FIG. 5 an enlarged perspective partial view of the device according to FIG. 4.

The device of FIG. 1 comprises a sample-taking means 10, a cartridge 30, a testing means 40 and a housing 50. As is indicated by the dashed lines, first the cartridge 30 is introduced into the tube-shaped housing 50 and subsequently the sample-taking means 10 is introduced into the housing 50 from the same side. A testing means 40 is introduced at the opposite side of the housing 50. Preferably, the cartridge 30 and/or the testing means 40 is displaceable within the housing 50 and secured against failing out.

Preferably, the device is constructed in the above-described manner and provided to a user for taking a sample and examination thereof. This arrangement represents a test kit which can be used in a simple manner and can also be handled by laypersons, in particular elderly people.

Figure 2:
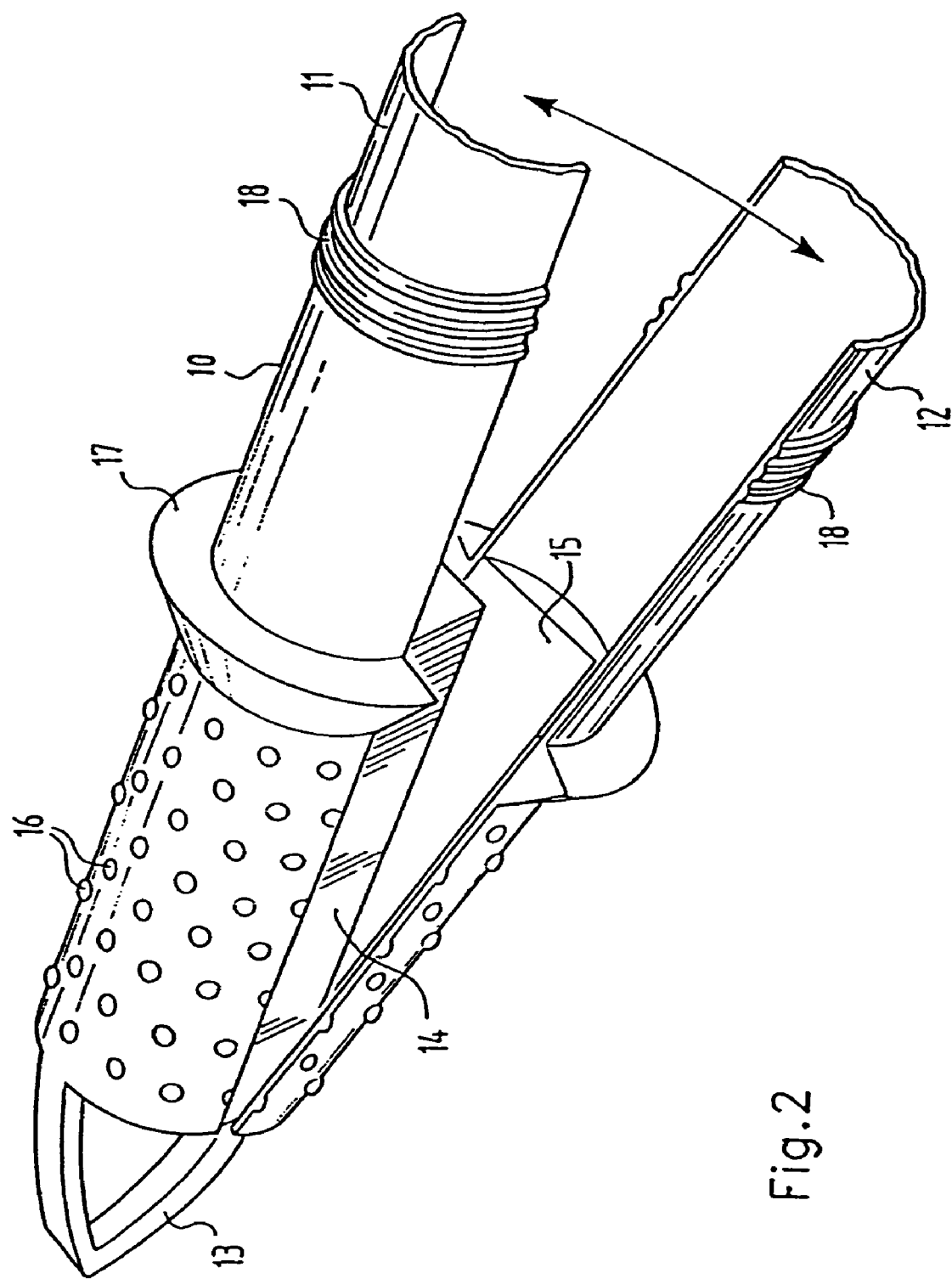

As shown in FIG. 2, the sample-taking means 10 consists of two half-tubes 11, 12 which form a tube (cylindrical cavity) when they are closed. The two half-tubes are connected with each other at one end (handle-facing end) by means of an elastic web 13 the stress of which presses the two halves apart so that they form a "V" when they are unstressed. In an alternative embodiment, the two half-tubes can be connected by a joint, wherein preferably the joint connection comprises a film hinge. For example, the film hinge can be arranged in a web connection between the half-tubes. Preferably, the web connection Is shaped similar to the web 13 in FIG. 2 and the film hinge is arranged in the area of the pointed end. In this embodiment both half-tubes can be freely pivoted with respect to each other. If a spring action is desired, additional spring means can be provided. At the inner surface of the one half-tube 11 a triangular oblong recess 14 Is arranged which can be engaged with a corresponding counter groove 15 formed at the other half-tube 12. The recess 14 and the counter groove 15 form a guide which prevents the two half-tubes from moving out in the lateral direction when the sample-taking means Is closed. At the handle-facing end of the outer surface of the half-tubes, a handling surface Is provided with nubs 16 which prevent gliding-off during use. The handling surface is closed at the sample-facing side by a funnel-shaped, peripheral edge 17 which helps to avoid a contact with surplus sample material. At the sample-facing side of the peripheral edge 17 a steep thread 18 is formed at the outer surface of the tube consisting of the two half-tubes.

Figure 3:
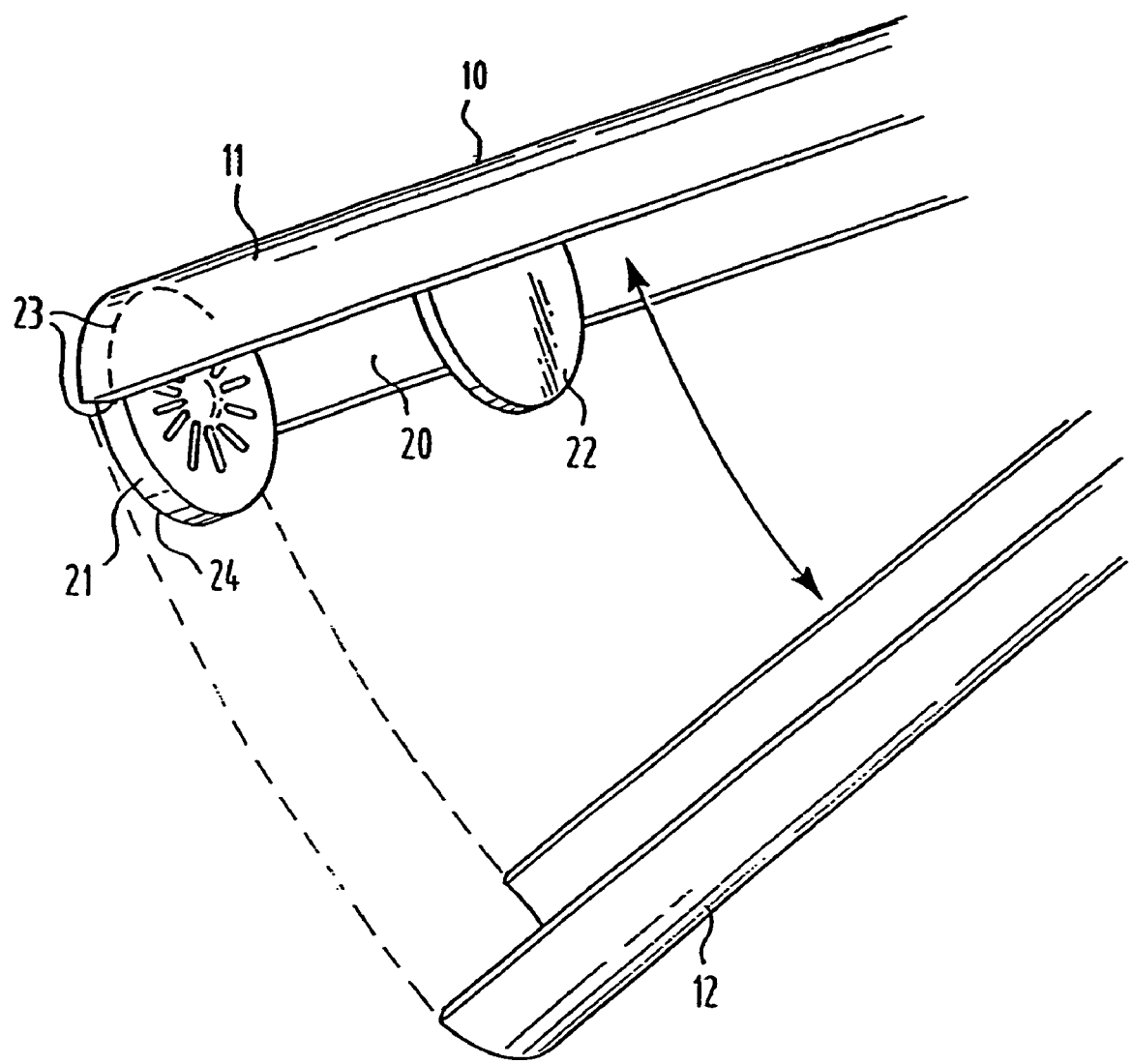

As shown in FIG. 3, at the sample-facing end of the sample-taking means 10 a first disk 21 is arranged at the one half-tube 12 and, spaced therefrom, a second disk 22. When closing the sample-taking means, i.e. when the two half-tubes 11, 12 contact each other, said two disks form a sample chamber 20. From the distance a between the two disks and the radius r of the half-tubes, the sample volume V to be taken is calculated as follows: $V = \pi \cdot r^2 \cdot a$. The length of the half-tubes 11, 12 is dimensioned such that between the handle-facing disk 22 and the above-described guide 14, 15 there is a sufficient space for optionally surplus sample material.

The sample-facing end disk 21 is connected to the inner surface of the half-tube 11 such that the connection resists to the forces caused during sample-taking; however, the disk 21 is broken out during introduction into the housing at one or a plurality of predetermined breaking points 23 by a resistance caused in the housing. A cone-shaped ring 24, the function of which is explained in more detail below, is attached to the outer edge of said disk 21. An indentation 25 is formed in the center of the disk 21. The area formed by this indentation corresponds to an opening of a truncated cone at the cartridge. Outside the indentation 25 the disk 21 has openings, so that a sieve 26 for mechanically opening the sample is realized. Instead of the indentation 25 a web, which will be described in more detail below, can be provided.

The handle4acing disk 22 is rigidly attached so that it resists to all forces caused during sample-taking and sample-processing.

Figure 4:
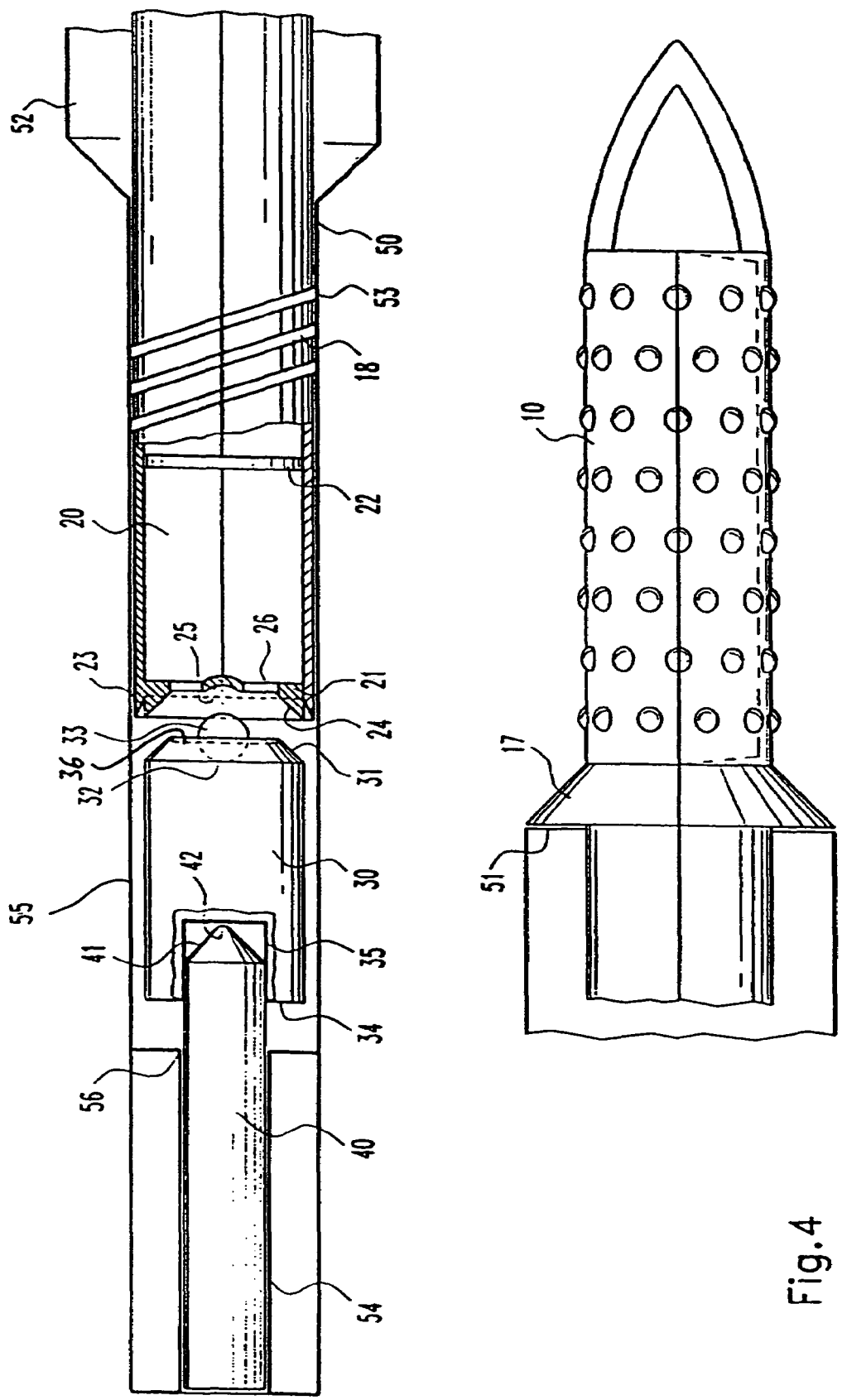

With further reference to FIG. 4, the cartridge 30 is at first described in more detail. The cartridge 30 contains a liquid which is used, for example, for diluting and chemically opening the sample. The size of the interior space of the cartridge 30 and the amount of liquid M are selected such that the cartridge can take up the sample volume V in addition to the liquid already contained in the cartridge. The liquid amount M is provided in an exactly dosed relationship with respect to the given sample volume. The cartridge is shaped like a cylinder. At the edge facing the sample-taking means, the cylinder tapers so as to form a truncated cone 31; thus, the sieve 26 of the sample-taking means comprising the cone-shaped ring 24 centers itself on the cartridge. This cone-shaped seat preferably serves at the same time as a seal between the sample-taking means and the cartridge. At the end of the truncated cone of the cartridge, a circular impression 36 having an opening 32 in its center is formed. The opening is closed by a metal ball 33 arranged therein. The metal ball 33 is arranged in the opening for example by shrinking it on. In this case, the size of the metal ball 33 is slightly larger than the opening 32 at the cone-shaped end so that the ball can be pressed into the cartridge 30 when introducing the sample-taking means into the housing. Either the indentation 25 or a web arranged on the sieve is used for pressing the ball 33 in. A web is particularly advantageous if the ball is arranged in the cover surface of the cartridge in a recessed manner. The dimensions are selected such that preferably the cone surfaces are in a sealing contact as soon as the ball has been pressed completely into the cartridge.

The opposite end of the cylindrical cartridge 30 is closed by a bottom 34 in the center of which there is an impression 35 which is also cylindrical and projects into the cartridge 30. Said impression 35 serves for taking up the testing means 40, The impression and the testing means are realized such that the wall of the impression 35 can be broken, and thus the content of the cartridge can be brought in contact with a test strip contained in the testing means.

The testing means 40 has the shape of a cylinder and its cartridge-facing end tapers so as to form a truncated cone 41. At the tip of the truncated cone there is an opening 42 through which sample solution can enter. An absorbent material is introduced into the truncated cone, said absorbent material transporting the sample fluid to the test strip (not shown) by capillary forces. The cylindrical testing means 40 comprises one or a plurality of recesses so that color reactions of the test strip can be observed as a result of the test. The closing material is preferably a porous, water-repellent material which prevents the sample fluid from penetrating the lasting means but which, however, allows the air displaced by the sample fluid to escape.

The housing 50 serves for receiving, protecting and coordinating the above-described three components, i.e. the sample-taking means 10, the cartridge 30 and the testing means 40. It consists of a tube, the interior of which is divided into different diameters and the front portion of which has a thread 53. In the present embodiment, the front end serving as the introduction opening is funnel-shaped, has a high edge and preferably a considerably larger diameter than the sample-facing end of the sample-taking means. The frontal end 51 of the housing contacts the funnel-shaped, peripheral edge 17 and closes the introduction opening. Thus, a stripping chamber 52 is formed in which surplus sample material contained on the outer surface of the sample-facing end of the sample-taking means is stripped off and disposed. Following the stripping chamber 52, the diameter of the tube decreases so that the sample-facing end of the sample-taking means remains closed and can be displaced until it engages with a thread 53 at the inner surface of this portion. At the other part of the housing a sample-taking space 54 is provided which is adapted to the size and shape of the testing device 40 such that the tubular testing means 40 is held in it but can be moved back and forth when a slight pressure is applied. The center portion 55 contains the cartridge 30 which is held only by the testing means and hangs freely in any other respect and which can be displaced together with the testing means 40.

By means of the above-described device, a test is carried out as follows.

Figure 5:
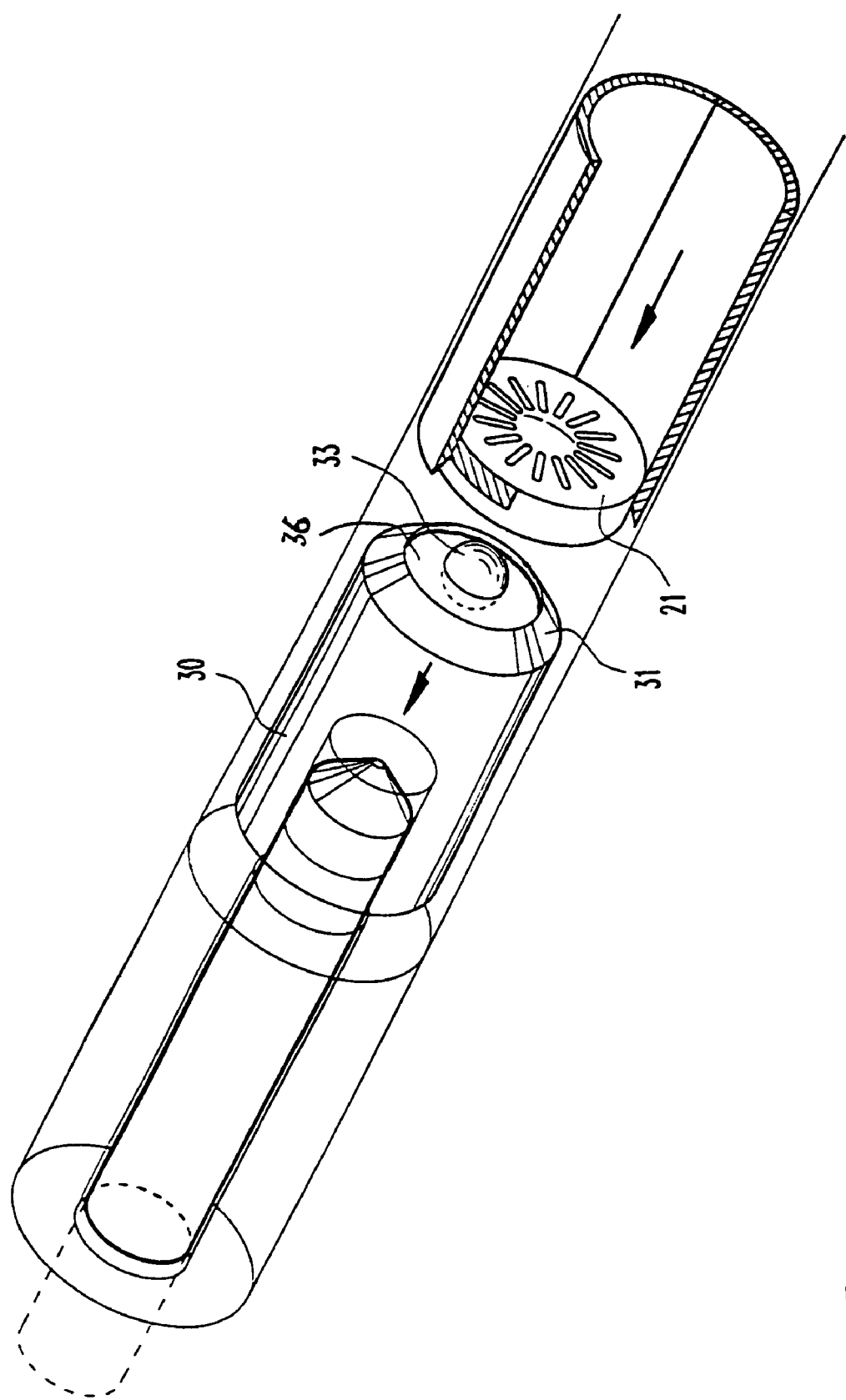

The test arrangement is mounted as follows. The sample-taking means 10 is removably inserted in the housing 50. The testing means 40 and the cartridge 30 are fitted into each other. The combination of the two is fixed in the rear part of the housing 50. The user removes the sample-taking means from the housing 50. If the connection between the half-tubes comprises an elastic web 13, the sample-taking means opens automatically. If a joint is provided, e.g. a film hinge, the user moves the half-tubes apart The two half-tubes 11 and 12 form a "V". In the area of the sample chamber 20, the sample substance is now held and fixed. By pressing the half-tubes together, the front edge of the sieve 26 mounted on the front end penetrates the sample and is held by the second half-tube on the opposite side. During the process of pressing the half-tubes together, the triangular projection 14 and the counter groove 15 engage with each other, a shearing action is prevented, and the two half-tubes 11, 12 close in a form-fit manner to form a complete tube. The sample substance is contained in the sample chamber 20. The sample chamber contains an exactly defined amount, optional surplus sample material is contained in the rear part of the sample-taking means, i.e. the surplus chamber. The sample-taking means is now introduced into the housing and centered to the middle by the funnel-shaped end portion of the stripping chamber 52. The sample-taking means is introduced until the external thread 18 contacts the internal thread 53. The semi-spherical indentation 25 of the front sieve 26 now contacts the closure ball 33 of the cartridge 30. The sample-taking means is now screwed Into the housing; thus, the cartridge 30, which is held by the testing means 40 and pushed by the sieve 26, moves backwards (cf. FIG. 5). The tapering portion 56 for the testing means serves as a stopper for the cartridge, and the cartridge is fixed there. By this process, the testing means is also moved backwards and projects from the rear end of the housing. The fact that the combination cartridge/testing means is moved outwards to the back until ft is actually fixed, prevents an early, undesired activation of the test strip. During the further turning movement, the closing ball 33 is pressed into the cartridge 30 by the sieve 26. The sieve 26 is then fixed on the cartridge 30 by the now meshing cone. By the arising pressure onto the sieve 26, the predetermined breaking point 23 is broken, the free sieve 26 is pressed onto the cartridge 30 by the sample. Then the sample is pressed into the cartridge 30 by the counter pressure of the separating wall 22 between sample chamber and surplus chamber through the sieve 26, the space formed by the impression 36, and the opening 32.

After termination of this process, the sample is contained in the cartridge 30 which is closed by the sieve 26 leaning on ft and the separating wall 22 pressing against ft.

In order to finally mix the sample, which has already been slightly stirred by the sieve 26, with the liquid contained in the cartridge 30, the entire testing apparatus is now shaken. The closing ball 33 located in the interior of the cartridge 30 is now used as a mixing ball, which also becomes acoustically noticeable by a rattling noise. When the noise level decreases, the user can assume that the sample has sufficiently mixed with the liquid and slows down the ball due to its higher viscosity.

The next step consists of activating the testing means projecting from the rear end of the housing. It functions as with a ball pen by quickly pressing the end of the testing means. During this process the membrane in the rear surface of the cartridge 30 is penetrated by the cone-shaped end 41 of the testing means. The liquid in the cartridge 30 passes through the hole 42 in the cone tip 41 into the interior of the testing means. A nonwoven arranged therein absorbs the liquid until it is saturated. A test strip arranged on this nonwoven is activated by the liquid and can subsequently be evaluated. The test result can be seen through a window or through a transparent design of the end of the testing means. In the scope of the invention, testing means can be used in which other ways of bringing the test strip (or the test substance) into contact with the sample mixture can be realized. As an alternative to the above-described embodiment, the cartridge can for example be realized such that it does not have an impression in the area of the bottom. In this case, an opening in the bottom is provided with a destroyable foil or sheet. After the foil or sheet has been destroyed, the sample mixture is forwarded to the test strip which optionally indicates a reaction. The above-mentioned foil or sheet is preferably an aluminum sheet or a multi-layer composite material which preferably comprises aluminum and plastics layers.

Preferably, the three components which the user can see, i.e. the sample-taking means, the housing and the testing means, are characterized by different colors. The components of the device according to the invention are preferably put to the user's disposal as a kit. For example, the mentioned components can be provided in one pack, e.g. a blister pack, separately from each other and ready for use.

In the meaning of the invention a) "variable coloring" means both different coloring and the variably strong coloring of the corresponding individual component by means of a selected individual color, and b) kit means a pack for producing a ready-to-use device for taking and examining samples.

It is an advantage of the device according to the invention that layperson can use it safely. In particular, penetration of sample material and the liquid contained in the cartridge, which can be toxic or caustic, is reliably avoided.

Moreover, the variable coloring supports the fact that the components are put together in the correct order.

In addition, a hygienic usability is ensured. Due to the integrated taking, processing and application of the sample, a defined relationship of sample amount and reagent amount is ensured.

Preferably, the components are produced from a plastic material which is suitable for the respective purpose. ABS is the material preferably used. In this case, the components are preferably produced by injection molding.

The described embodiments show only examples for the realization of the invention. The person skilled in the art can carry out constructional and functional modifications of the embodiments.

The invention claimed is:

1. A device for taking and examining samples, comprising a housing having positioned therein a cartridge containing a liquid, a testing means, and a sample-taking means, the sample-taking means comprising two half-tubes connected to each other at one end, the two half-tubes are capable of pivoting between two positions, an open position, wherein the two half-tubes are apart for collecting a sample and a closed position, wherein the two half-tubes are pressed together, wherein the cartridge is displaceable within the housing such that a sample introduced by the sample-taking means is operable to form a sample mixture with the liquid within the cartridge, and wherein the testing means is displaceable within the housing.

2. The device according to claim 1, wherein at least one of the two half-tubes comprises a first disk and a second disk defining a sample chamber, when the two-half tubes are in the closed position.

3. The device according to claim 2, wherein the first disk comprises a sieve and an indentation, and further wherein an edge of the first disk comprises a cone-shaped ring.

4. The device according to claim 3, wherein the cartridge is cylindrically shaped and comprises, on one end, a truncated cone engageable with the cone-shaped ring.

5. The device of claim 1, wherein the joint is selected from the group consisting of a film hinge and an elastic web.

6. The device of claim 2, wherein the first disk is coupled to the sample-taking means with predetermined breaking points.

7. The device according to claim 1, wherein the testing means is displaceable within the housing between a first position, in which the testing means does not contact the sample mixture, and a second position, in which the testing means makes contact with the sample mixture.

* * * * *